United States Patent [19]

Stolowitz

[11] Patent Number: 5,852,178
[45] Date of Patent: *Dec. 22, 1998

[54] PHENYLBORONIC ACID COMPLEXING REAGENTS FOR CONJUGATING BIOLOGICALLY ACTIVE MOLECULES

[75] Inventor: Mark L. Stolowitz, Long Beach, Calif.

[73] Assignee: Prolinx, Inc., Bothell, Wash.

[*] Notice: The term of this patent shall not extend beyond the expiration date of Pat. Nos. 5,594,111, 5,594,151 and 5,623,055.

[21] Appl. No.: 577,068

[22] Filed: Dec. 22, 1995

Related U.S. Application Data

[63] Continuation of Ser. No. 188,460, Jan. 28, 1994, abandoned.
[51] Int. Cl.$^6$ .............................. C07K 17/06; C07K 1/10; C12N 11/06; G01N 33/549
[52] U.S. Cl. .......................... 530/402; 435/174; 435/181; 436/518; 436/532; 530/810; 530/816; 568/288; 568/289
[58] Field of Search ...................................... 435/174, 180, 435/181; 436/518, 532; 530/412, 413, 415, 816, 810, 402; 564/443; 568/288, 289

[56] References Cited

U.S. PATENT DOCUMENTS

| | | | |
|---|---|---|---|
| 2,548,257 | 7/1951 | Goldberg, et al. | 260/519 |
| 4,269,605 | 5/1981 | Dean et al. | 23/230 B |
| 4,281,181 | 7/1981 | Nagasawa et al. | 562/453 |
| 4,496,722 | 1/1985 | Gallop et al. | 544/69 |
| 4,713,346 | 12/1987 | Gallop et al. | 436/86 |
| 4,783,487 | 11/1988 | Brune | 514/563 |
| 4,851,443 | 7/1989 | Brune | 514/563 |
| 4,894,229 | 1/1990 | Polson et al. | 424/92 |
| 4,910,300 | 3/1990 | Urdea et al. | 536/287 |
| 5,002,883 | 3/1991 | Bieniarz et al. | 435/176 |
| 5,045,451 | 9/1991 | Uhr et al. | 435/7.23 |
| 5,093,232 | 3/1992 | Urdea et al. | 435/6 |
| 5,183,653 | 2/1993 | Linder et al. | 424/1.1 |
| 5,242,842 | 9/1993 | Sundrehagen | 436/536 |
| 5,594,111 | 1/1997 | Stolomitz | 530/391.1 |
| 5,594,151 | 1/1997 | Stolomitz | 548/542 |
| 5,623,055 | 4/1997 | Stolomitz | 530/391.1 |

FOREIGN PATENT DOCUMENTS

| | | |
|---|---|---|
| 9013818 | 11/1990 | WIPO. |
| 9208722 | 5/1992 | WIPO. |
| 9420858 | 9/1994 | WIPO. |

OTHER PUBLICATIONS

Imagawa et al., Journal of Applied Biochemistry, vol. 4, 1982, pp. 41–57.
Kliegel et al., Monatsh. Chem. 114(4), 1983, pp. 465–484.
Wilcheck, M. & Bayer, E.A.; "Introduction to Avidin–Biotin Technology"; *Methods in Enzymology*; vol. 184; 1990 (USA).
Kessler et al.; "Non-radioactive Labeling and Detection of Nucleic Acids"; *Biol. Chem. Hoppe–Seyler*; vol. 371, pp. 917–927; 1990 (USA).
Singhal, R.P. & DeSilva, S.S.M.; "Boronate Affinity Chromatography"; *Advances in Chromatography*; vol. 31, pp. 293–335; 1992 (USA).
Mazzeo, J.R. & Krull, I.S.; "Immobilized Boronates for the Isolation and Separation of Bioanalytes"; *Biochromatography*; vol. 4, pp. 124–130; 1989.
Bergold, A & Scouten, W.H.; "Borate Chromatography"; *Solid Phase Biochemistry*; Ch. 4, pp. 149–187; 1983 (USA).
Lorand, J.P. & Edwards, J.O.; "Polyol Complexes and Structure of the Benzeneboronate Ion"; *J. Org. Chem.*; vol. 24, p. 769; 1959 (USA).
Bowie, R.A. & Musgrave, O.C.; "Organoboron Compounds. Part V.* The Hydrolysis of Cyclic Phenylboronates"; *J. Amer. Chem. Soc.*; pp. 3945–3949; 1963 (USA).
Sienkiewicz, P.A. & Roberts, D.C.; "pH Dependence of Boronic Acid–Diol Affinity in Aqueous Solution"; *J. Inorg. Nucl. Chem.*; vol. 42, pp. 1559–1571; 1980 (USA).
Tanner, D.W. & Bruice, T.C.; "Boric Acid Esters" *J. Amer. Chem. Soc.*; vol. 89, pp. 6954–6971; 1967 (USA).
Kessler, C.; *Advances in Mutagenesis Research* (Obe, G. ed.); pp. 105–152; Springer–Verlag, Berlin/Heidelberg; 1990 (USA).
Brinkley, M.; "A Brief Survey of Methods for Preparing Protein Conjugates with Dyes, Haptens, and Cross Linking Reagents"; *Bioconjugate Chem.*; vol. 3, pp. 2–13; 1992 (USA).

(List continued on next page.)

*Primary Examiner*—David M. Naff
*Attorney, Agent, or Firm*—Blakely, Sokoloff, Taylor & Zafman

[57] ABSTRACT

A new class of phenylboronic acid complexing reagents are provided capable of binding with phenylboronic acids is disclosed having one of the following structures:

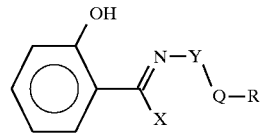

General Formula I

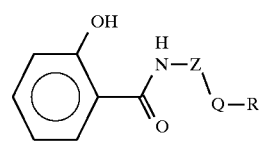

General Formula II wherein group X is selected from H, $CH_3$ and $C_6H_5$; and groups Y and Z are selected from O and $CH_2$; group Q is a spacer which is from 2 to 12 carbon equivalents in length, and which may contain intermediate amide and/or ether functionalities; and group R is a reactive electrophilic moiety suitable for conjugation of a phenylboronic acid complexing reagent with a biological macromolecular species, low molecular weight species or solid phase support having a reactive pendant nucleophilic moiety. The phenylboronic acid complexing reagents are utilized in conjunction with phenylboronic acid reagents to facilitate chemical conjugation without the use of intermediary biological macromolecules. The method of making and using such reagents is also disclosed.

5 Claims, 8 Drawing Sheets

OTHER PUBLICATIONS

Linder et al.; "Technetium Labeling of Monoclonal Antibodies with Functionalized BATOs 1. TcCl(DMG)₃PITC"; *Bioconjugate Chem.*; vol. 2, pp. 160–170; 1991 (USA).

Linder et al.; "Technetium Labeling of Monoclonal Antibodies with Functionalzied BATOs 2. TcCl(DMG)₃CPITC Labeling of B72.3, etc." *Bioconjugate Chem.*; vol. 2, pp. 407–415; 1991 (USA).

Burnett et al.; "Synthesis of a Fluorscent Boronic Acid Which Reversibly Binds to Cell Walls, etc."; *Biochem. Biophys. Research Commun.*; vol. 96, pp. 157–162; 1980 (USA).

Borrebaeck, C.; "Strategy for the Production of Human Monoclonal Antibodies Using In Vitro Activated B Cells"; *Journal of Immunological Methods*; vol. 123, pp. 157–165; 1989 (USA).

Steinberg, G.M. & Swidler, R.; "The Benzohydroxamate Anion"; *J. Org. Chem. vol.*; vol. 30, pp. 2362–2365; 1965 (USA).

Bauer, L. & Exner, O.; "The Chemistry of Hydroxamic Acids and N–Hydroxyimides"; *Angew. Chem. Internat. Edit.*; vol. 13, pp. 376–384; 1974 (USA).

Cai, S.X. & Kean, J.; "o–Acetomidophenylboronate Esters Stabilized Toward Hydrolysis by an Intramolecular O–B Interation, etc."; *Bioconjugate Chem.*; vol. 2, pp. 317–322; 1991 (USA).

Ramalingam, K. & Nowotnik, D.; "Syntheses of Some Isothiocyanatophenylboronic Acids"; *Org. Prep. Proc. Int.*; vol. 23, 729–734; 1991 (USA).

Kliegel, W. & Nanninga, D.; "Borchelate Von Salicyladehydnitronen"; *Journal of Organometallic Chem.*; vol. 243, pp. 373–385; 1983 (USA).

Ripan et al.; "Etude Du Systeme Acide Borique–Salicylaldoxime en Solutions Aqueuses"; *Revue Roumaine de Chimie*; vol. 10, pp. 965–971; 1965 (FRA).

Roberts et al.; "Pluripotential Amino Acids"; *Tetrahedron Letters*; vol. 21, pp. 3435–3438; 1980 (USA).

Kemp, D.S. & Roberts, D.; "New Protective Groups for Peptide Synthesis—II The DOBZ Group, etc."; *Tetrahedron Letters*; vol. 52, pp. 4629–4632; 1975 (USA).

Kliegel, W. & Nanninga, D.; "Borchelate von N–substituierten Hydroxamsauren"; *Chem. Ber.*; vol. 116, pp. 2616–2629; 1983 (FRG).

Mikesova, M. & Bartusek, M.; "Reaction of Boric Acid with Salicylic and Chromotropic Acids and with Their Derivatives"; *Chem. Zvesti*; vol. 32(4), pp. 472–477; 1978.

Feeney, R.E., "Chemical Modification of Proteins: Comments and Perspectives"; *Int. J. Peptide Protein Res,*; vol. 29, pp. 145–161 (USA).

Means, G.E. & Feeney, R.E.; "Chemical Modifications of Proteins: History and Applications"; *Bioconjugate Chem.*; vol. 1, pp. 2–12 (USA).

O'Shannessy, D.J. & Quarles, R.H.; "Labeling of the Oligosaccharide Moieties of Immunoglobulins"; *J. Immunological Methods*; vol. 99, pp. 153–161 (1987) (USA).

van't Reit, B., Wampler, G.L.; & Elford, H.L.; "Synthesis of Hydroxy– and Amino–Substituted Benzohydroxamic Acids, etc."; *J. Medicinal Chem.*; vol. 22, No. 5, 589–592, 1979 (USA).

Soundararajan, et al.; "Boronic Acids for Affinity Chromatography: Spectral Methods for Determination, etc."; *Analytical Biochem.*; vol. 178, pp. 125–134, 1989 (USA).

Goodchild, J.; "Conjugates of Oligonucleotides and Modified Oligonucleotides: A Review of Their Synthesis and Properties"; *Bioconjugate Chem,*; vol. 1, No. 3, pp. 165–193, 1990 (USA).

Kessler, C.; *Nonradioactive Labeling and Detection of Biomolecules*; Ch. 1–3, 1992 (USA).

Meares, C.F., "Editorial: Introduction to Bioconjugate Chemistry"; *Bioconjugate Chem.*; vol. 1, No. 1, 1990 (USA).

Waggoner, A.S.; "Fluorescent Probes for Cytometry"; *Flow Cytometry and Sorting*; 2nd ed; pp. 209–225; 1990 (USA).

Chen, et al.; "Structure–Activity Relationships in a Series of 5–[(2,5–Dihydroxybenzyl)amino]salicylate, etc."; *Chemical Abstracts*; vol. 120; 322877v; 1994 (USA).

Hirano, et al.; "Silver halide color photographic material"; *Chemical Abstracts*; vol. 116; 140021u; 1992 (USA).

Kawasaki, et al.; "Silver halide photographic material with improved storage stability"; *Chemical Abstracts*; 109; 160505r; 1988 (USA).

Priewe, H., et al.; "o–Hydroxybenzohydroxamic Acids"; Chemical Abstracts; vol. 52; 10184; 1958 (USA).

PHENYLBORONIC ACID COMPLEXING REAGENTS FOR CONJUGATING BIOLOGICALLY ACTIVE MOLECULES

STATEMENT OF RELATED CASES

This Application is a continuation of application Ser. No. 08/188,460 filed on Jan. 28, 1994, now abandoned.

FIELD OF THE INVENTION

The present invention relates to the field of bioconjugate preparation, and more particularly, to a class of phenylboronic acid complexing reagents useful for the conjugation of biological macromolecules, and the method of making and using such reagents.

BACKGROUND OF THE INVENTION

Bioconjugation is a descriptive term for the joining of two or more different molecular species by chemical or biological means, in which at least one of the molecular species is a biological macromolecule. This includes, but is not limited to, conjugation of proteins, peptides, polysaccharides, hormones, nucleic acids, liposomes and cells, with each other or with any other molecular species that add useful properties, including, but not limited to, drugs, radionuclides, toxins, haptens, inhibitors, fluorophores, ligands, etc. Immobilization of biological macromolecules is also considered a special case of bioconjugation in which the macromolecule is conjugated, either reversibly or irreversibly, to an insoluble solid-phase support. Bioconjugation is used extensively in biochemical, immunochemical and molecuar biological research. Major medical and scientific applications of bioconjugation include detection of gene probes, enzyme-linked immuno solid-phase assay, monoclonal antibody drug targeting and medical imaging.

Avidin-Biotin System

Although numerous methods of bioconjugate preparation have been described, a significant number of those reported in the literature have been prepared by exploiting the Avidin-Biotin system, in which, the binding specificity of the protein Avidin (purified from egg white), or Streptavidin (purified from the bacterium *Streptomyces avidinii*), toward the cofactor Biotin (vitamin H) is utilized to bridge an Avidin conjugated macromolecule with a biotinylated macromolecule. Both Avidin and Streptavidin possess four Biotin binding sites of very high affinity ($K=10^{15}$ mol$^{-1}$). This system has been utilized extensively for enzyme-linked immuno solid-phase assay (ELISA), in which an enzyme-Avidin conjugate (useful for detection by reaction with the enzyme's substrate to afford a colored or chemiluminescent product) is employed to detect the presence of a biotinylated antibody, after first binding the antibody to an immobilized antigen or hapten. Applications of the Avidin-Biotin system number in the hundreds, and have recently been reviewed (Wilchek, M. and Bayer, E. A., *Methods in Enzymology*, 184 (1990)). Although utilized extensively, several limitations are known to be associated with the Avidin-Biotin system, which include nonspecific binding generally attributed to the basicity of the Avidin molecule, nonspecific binding attributed to the presence of carbohydrate residues on the Avidin molecule, and background interference associated with the presence of endogenous Biotin, which is ubiquitous in both eukaryotic and prokaryotic cells.

Digoxigenin-Anti-Digoxigenin System

An alternative bioconjugation system designed to overcome the limitations associated with the Avidin-Biotin system has recently been developed for the detection of gene probes by ELISA (Kessler, C., Holtke, H.-J., Seibl, R., Burg, J. and Muhlegger, K., *Biol. Chem. Hoppe-Seyler*, 371, 917–927 (1990)). This system involves the use of the steroid hapten Digoxigenin, an alkaloid occuring exclusively in Digitalis plants, and Fab fragments derived from polyclonal sheep antibodies against Digoxigenin (anti-Digoxigenin). The high specificity of the various anti-Digoxigenin antibodies affords low backgrounds and eliminates the non-specific binding observed in Avidin-Biotin systems. Digoxigenin-labeled DNA and RNA probes can detect single-copy sequences in human genomic Southern blots. Numerous applications of this system have recently been reported.

Immobilized Boronates

Phenylboronic acids are known to interact with a wide range of polar molecules having certain requisite functionalities. Complexes of varying stability, involving 1,2-diols, 1,3-diols, 1,2-hydroxy acids, 1,3-hydroxy acids, 1,2-hydroxylamines 1,3-hydroxylamines, and 1,2-diketones and 1,3-diketones, are known to form with either neutral phenylboronic acid or phenylboronate anion. Consequently, immobilized phenylboronic acids have been exploited as chromatographic media to selectively retain, from diverse biological samples, those molecular species having the requisite functionalities. Many important biological molecules including carbohydrates, catecholamines, prostaglandins, ribonucleosides, and steroids contain the requisite functionalities, and have been either analyzed or purified in this manner. The use of phenylboronic acid chromatographic media for the isolation and separation of various analytes has been reviewed (Singhal, R. P. and DeSilva, S. S. M. (1992) *Adv. Chromatog.*, 31, 293–335; Mazzeo, J. R. and Krull, I. S. (1989) *BioChromatog.*, 4, 124–130; and Bergold, A. and Scouten, W. H. (1983) in Solid Phase Biochemistry (Scouten, W. H. ed.) pp. 149–187, John Wiley & Sons, New York).

Phenylboronic acid, like boric acid, is a Lewis acid, and ionizes not by direct deprotonation, but by hydration and to give the tetrahedral phenylboronate anion ($pK_a=8.86$). Phenylboronic acid is three times as strong an acid as boric acid. Ionization of phenylboronic acid is an important factor in complexation, in that, upon ionization, boron changes from trigonal coordination (having average bond angles of 120° and average bond lengths of 1.37 Å) to the tetrahedrally coordinated anion (having average bond angles of 109° and average bond lengths of 1.48 Å).

Molecular species having cis or coaxial 1,2-diol and 1,3-diol functionalities, and particularly carbohydrates, are known to complex with immobilized phenylboronate anion, to form cyclic esters under alkaline aqueous conditions (Lorand, J. P. and Edwards, J. O. (1959) *J. Org. Chem.* 24, 769).

Acidification of the 1,2-diol and 1,3-diol complex releases the diol containing species, presumably due to hydrolysis of the cyclic ester, which is induced by ring-strain associated with a cyclic boronic acid ester involving trigonal coordinated boron. Coplaner aromatic 1,3-diols, like 1,8-dihydroxynaphthalene, are known to complex even under acidic conditions, presumably due to the hydrolytic stability of planar six-membered cyclic boronic acid esters (Bowie, R. A. and Musgrave, O. C. (1963) *J. Chem. Soc.*, 3945–3949, and Sienkiewicz, P. A. and Roberts, D. C. (1980) *J. Inorg. Nucl. Chem.*, 42, 1559–1571).

Theoretical studies have suggested that phenolic compounds having a variety of adjacent proton donor functionalities may complex with borate anion under alkaline aqueous conditions (Tanner, D. W. and Bruice, T. C. (1967) *J. Amer. Chem. Soc.,* 89, 6954).

Although immobilized phenylboronates have been utilized for chromatographic separation of biological molecules having the requisite functionalities, notwithstanding the substantial amount of research into bioconjugation, and the substantial amount of investment in this field, the selectivity of phenylboronic acid has not heretofore been exploited to enable the conjugation of biological macromolecules with one another or with other molecular species that add useful properties.

SUMMARY OF THE INVENTION

The present invention relates to a novel class of phenylboronic acid complexing reagents useful for the preparation of bioconjugates, and the method of making and using such reagents. In the present invention, in the place of prior art Avidin-Biotin and Digoxigenin-anti-Digoxigenin systems, phenylboronic acid complexing reagents are utilized in conjunction with prior art phenylboronic acid reagents to facilitate chemical conjugation without the use of intermediary biological macromolecules. Bioconjugate preparation often involves the conjugation of several components including, but not limited to, proteins, peptides, polysaccharides, hormones, nucleic acids, liposomes and cells, with each other or with any other molecular species that add useful properties, including, but not limited to, drugs, radionuclides, toxins, haptens, inhibitors, fluorophores, ligands, and solid-phase supports. These various components utilized in bioconjugate preparation will collectively be termed bioactive species (BAS).

Reagents suitable for the modification of a bioactive species for the purpose of incorporating a phenylboronic acid complexing moiety are selected from either General Formula I and General Formula II, set forth below.

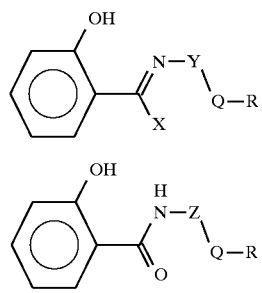

General Formula I

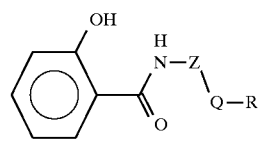

General Formula II

Reagents of General Formula I are those wherein X is selected from either H, $CH_3$ and $C_6H_5$, and wherein Y is selected from either O and $CH_2$. Reagents of General Formula II are those wherein group Z is selected from either O and $CH_2$. In both General Formulas I and II, group Q comprises a spacer which seperates either group Y, or group Z, from group R. In both General Formulas I and II, group R is a reactive electrophilic moiety suitable for reaction of the phenylboronic acid complexing reagent with a bioactive species.

Reagents of General Formula I are preferably those wherein group X is selected from either H and $CH_3$, and group Y is O. Reagents of General Formula II are preferably those wherein group Z is O. In both General Formulas I and II, group Q is preferably selected from either an alkyl chain or polyether chain, of from 2 to 12 carbon equivalents in length, and which may contain intermediate amide functionalities, and is preferably $(CH_2)_n$, wherein n=2 to 6, or $(CH_2CH_2O)_n$, wherein n=2 to 4. In both General Formulas I and II, group R is preferably selected from, but is not limited to, either hydrazide, isothiocyanate, N-hydroxysuccinimidyl ester, N-hydroxysulfosuccinimidyl ester, imidate ester, 2,2,2-trifluoroethanesulfonyl, bromoacetamide, iodoacetamide, maleimide and 2-cyanoethyl-N,N-diisopropylphosphoramidite ester moieties.

Reaction of a reagent of General Formula I with a bioactive species affords a semiconjugate having pendant phenylboronic acid complexing moieties (one or more) of General Formula III, wherein the symbol labeled BAS represents the bioactive species, and wherein groups X, Y and Q are as were previously defined.

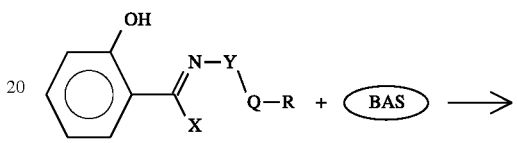

General Formula I

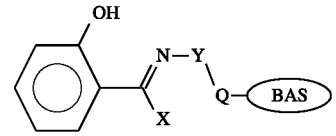

General Formula III

Reaction of a reagent of General Formula II with a bioactive species affords a semiconjugate having a pendant phenylboronic acid complexing moieties (one or more) of General Formula IV, wherein the symbol labeled BAS represents the bioactive species, and wherein groups Z and Q are as were previously defined.

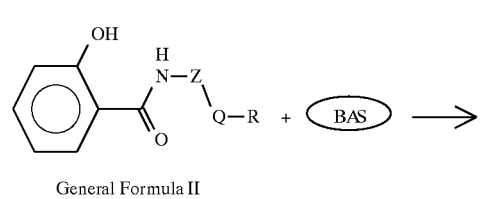

General Formula II

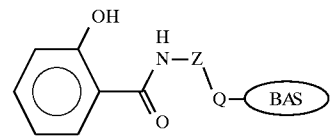

General Formula IV

Similarly, phenylboronic acid reagents, described in greater detail in my copending application, "Phenylboronic Acid Complexes Derived from Aminosalicylic Acid for Bioconjugate Preparation", Ser. No. 08/189,176, filed Jan. 28, 1994, now U.S. Pat. No. 5,623,055, may be appended to a bioactive species to afford a semiconjugate having pendant phenylboronic acid moieties (one or more) of General Formula V, wherein the symbol labeled BASII represents a second bioactive species, differing from the bioactive species labeled BAS.

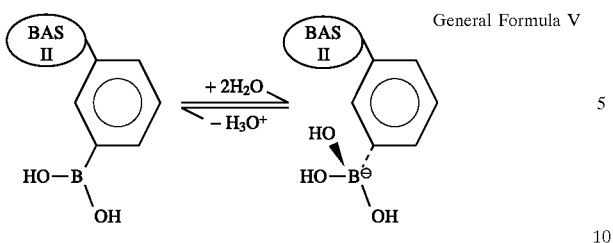

General Formula V

A semiconjugate of General Formula III, prepared from bioactive species BAS and having pendent phenylboronic acid complexing moities, may be complexed with a semiconjugate of General Formula V, prepared from a second bioactive species BASII and having pendant phenylboronic acid moities, to afford a bioconjugate of General Formula VI, wherein the symbols labeled BAS and BASII, and wherein groups X, Y and Q are as were previously defined.

In this manner, biological macromolecules may be conjugated to one another or to other functionalities which impart useful properties.

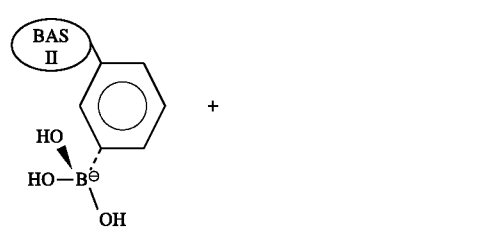

General Formula V

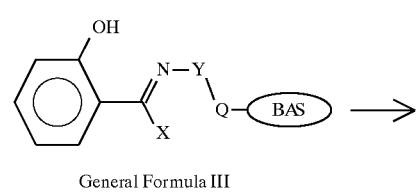

General Formula III

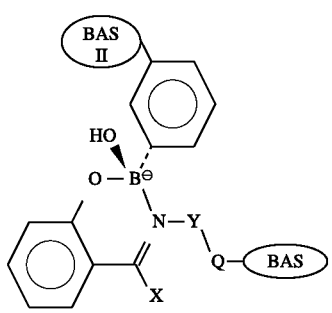

General Formula VI

Similarly, a semiconjugate of General Formula IV, prepared from a bioactive species BAS and having pendent phenylboronic acid complexing moities, may be complexed with a semiconjugate of General Formula V, prepared from a second bioactive species BASII and having pendant phenylboronic acid moities, to afford a bioconjugate of General Formula VII, wherein the symbols labelled BAS and BASII, and wherein groups Z and Q are as were previously defined.

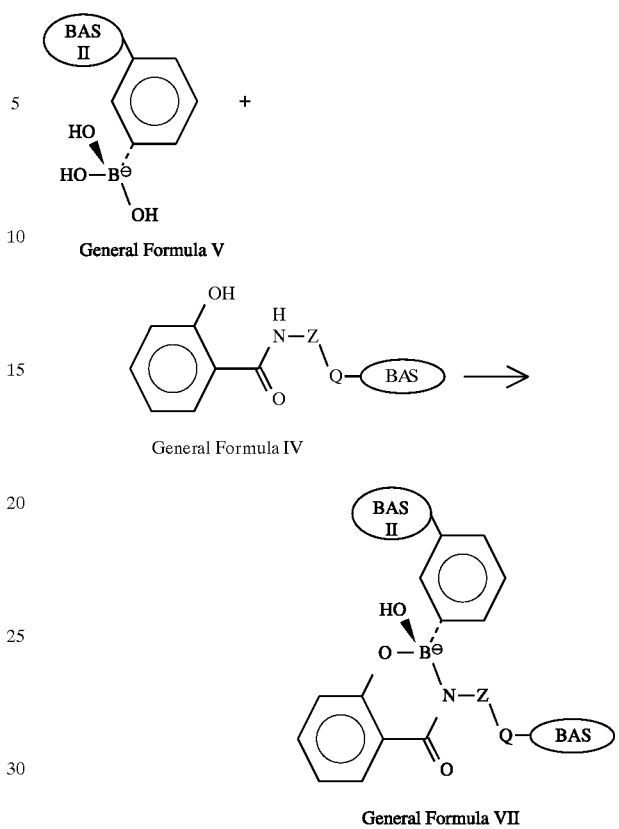

General Formula V

General Formula IV

General Formula VII

Bioconjugates of General Formulas VI and VII may be prepared in buffered aqueous or aqueous/organic solutions. The bioconjugate is formed within a few minutes at room temperature. The stability of the bioconjugate at a given pH is determined by substituent groups X, Y and Z. For all groups X, Y and Z, conjugates are stable in buffered alkaline aqueous solutions over the approximate pH range 8.5 to 11.5. Bioconjugates of General Formula VII, wherein group Z is O, are stable in buffered aqueous solutions over the broad approximate pH range 2.5 to 11.5. The bioconjugation reaction (phenylboronic acid complexation) is insensitive to significant variations in ionic strength, temperature, the presence of organic solvents, and the presence of chaotropic agents (protein denaturants), which are incompatible with prior art systems wherein the structure of a biological macromolecule must be maintained to preserve requisite binding properties. In most instances, the constraints governing the formation of bioconjugates, by the system herein described, are limited to those imposed by the conditions requiered to maintain viability of the bioactive species.

BREIF DESCRIPTION OF THE DRAWINGS

DETAILED DESCRIPTION

Synthesis of Phenylboronic Acid Complexing Reagents of General Formula I

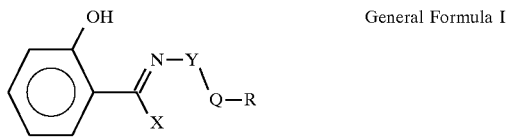

General Formula I

Figure 1A:
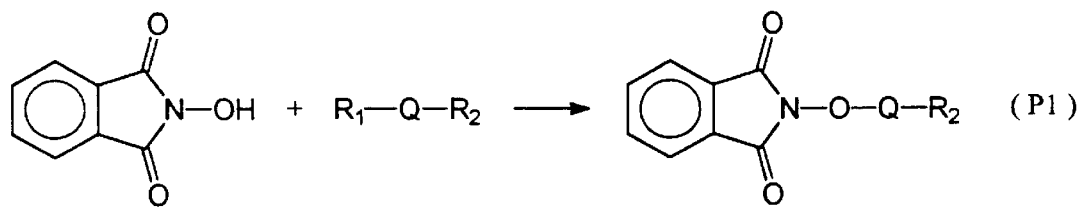
FIGS. 1A and 1B illustrate the synthesis of compounds of General Formula I, wherein X is selected from either H, $CH_3$, and $C_6H_5$, and wherein Y is 0.
Figure 1A:
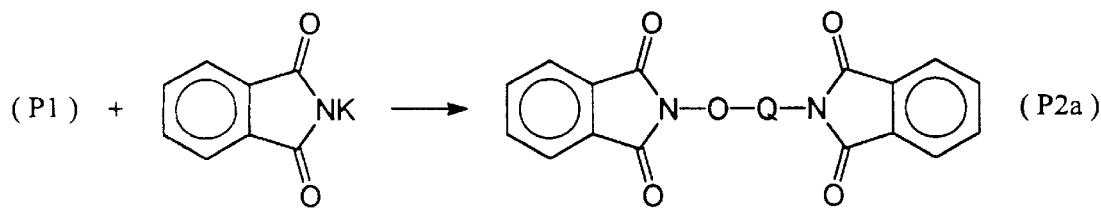
Figure 1A:
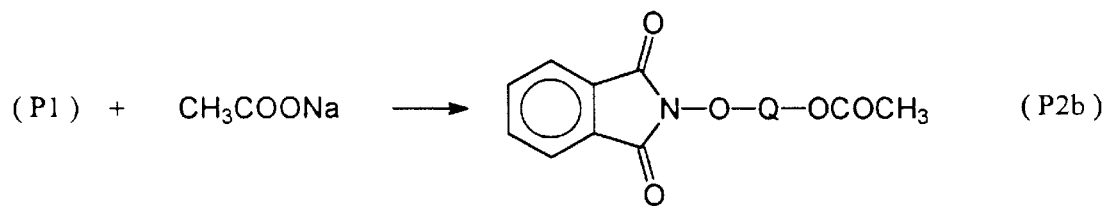
Figure 1A:
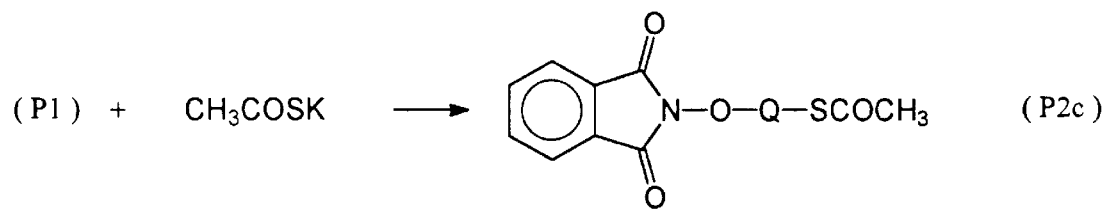
Figure 1A:
Figure 1A:
Figure 1B:
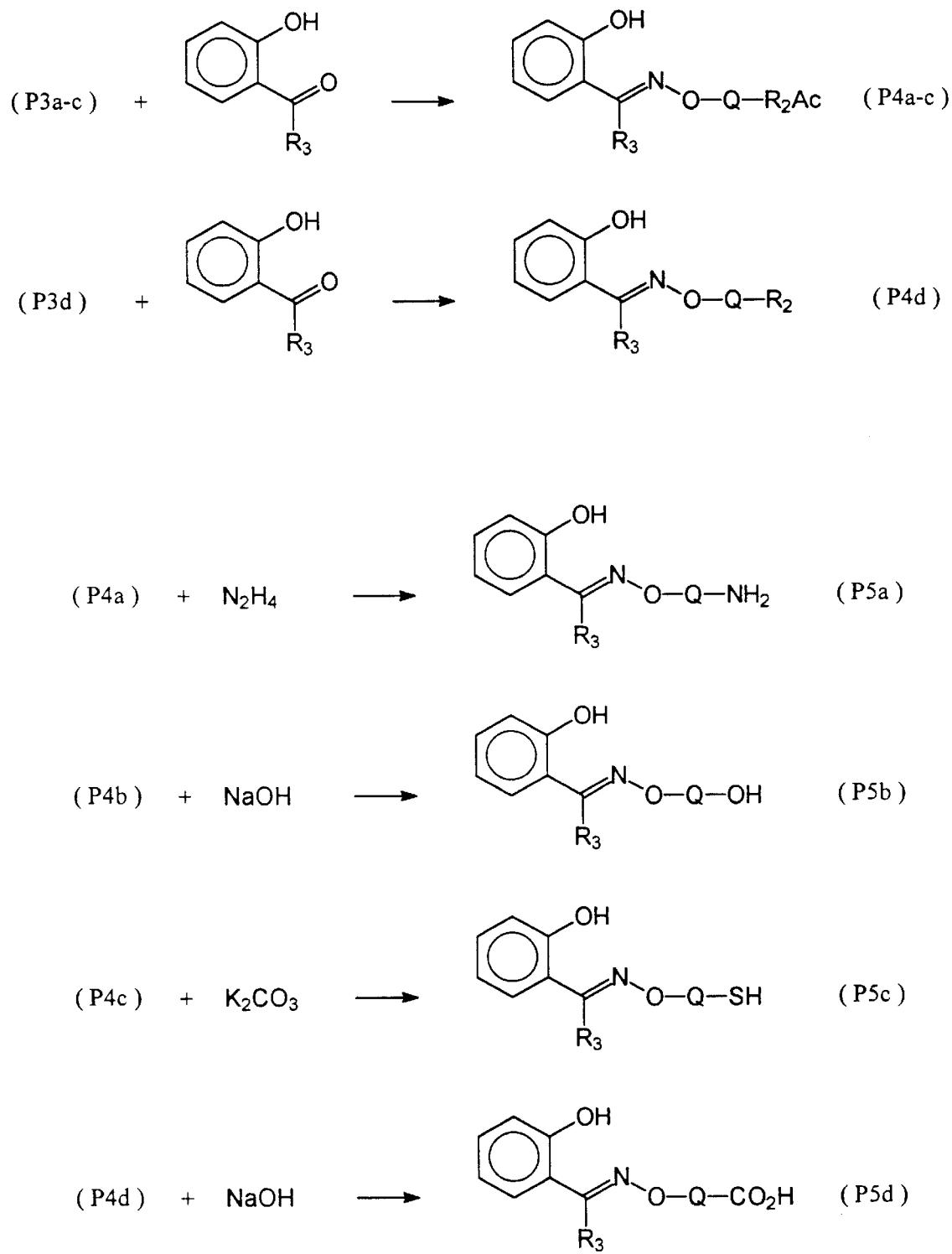

As illustrated in FIGS. 1A and 1B, reagents of General Formula I, wherein X is selected from either H, $CH_3$ and $C_6H_5$, and wherein Y is O, are prepared by condensation of N-hydroxyphthalimide with a compound of the general formula $R_1$—Q—$R_2$, wherein $R_1$ is selected from either Br, Cl and I, and is preferably Br, and wherein $R_2$ is selected form either Br, Cl, I, $CO_2H$ and $CO_2CH_3$, and is preferably selected from either Br, $CO_2H$ and $CO_2CH_3$, and wherein Q is a spacer which is selected from either an alkyl chain or polyether chain, of from 2 to 12 carbon equivalents in length, and which may contain intermediate amide functionalities, and is preferably $(CH_2)_n$, wherein n=2 to 6, or $(CH_2CH_2O)_n$, wherein n=2 to 4.

In the initial reaction, a compound of the general formula $R_1$—Q—$R_2$ is heated in dimethylforamide with one equivalent of N-hydroxyphthalimide at from 40° to 100° C. until solution is obtained. The solution is then allowed to cool to room temperature at one equivalent of triethylamine added, producing a dark red color associated with the N-hydroxyphthalimide anion. The solution is stirred at room temperature for from one to four days, the progress of the reaction being monitored by thin-layer chromatography (TLC). Upon completion of the reaction, water is added to effect precipitation of the product, which is washed with water and dried at room temperature, to afford a product of the general formula P1, wherein Q and $R_2$ are as were previously defined.

The product of the general formula P1, wherein $R_2$ is selected from either Br, Cl and I, is condensed with a reagent preferably selected from, but not limited to, $C_6H_4(CO)_2NK$, $CH_3COONa$ and $CH_3COSK$, to afford products of general formula P2 (FIG. 1A, P2a–c), wherein group Q is as was previously defined. Conditions vary depending upon the choice of desired product, but generally involve the addition of 1.1 equivalents of either $C_6H_4(CO)_2NK$, $CH_3COONa$ or $CH_3COSK$ to a product of the general formula P1 by refluxing in a polar solvent selected from either acetic acid, dimethylformamide, methanol or ethanol, for from 1 to 24 hours.

Products of general formula P2 are subjected to acid catalyzed hydrolysis of the phthalimide group to afford products of general formula P3 (FIG. 1B, P3a–d), wherein $R_2Ac$ is selected from either $N(CO)_2C_6H_4$, $OCOCH_3$ and $SCOCH_3$, and wherein Q is as was previously defined. Acid catalyzed hydrolysis of the phthalimide group in a product of the general formula P2d, wherein $R_2$ is $CO_2CH_3$, affords a product of the general formula P3d, wherein $R_2$ is selected from either $CO_2H$ and $CO_2CH_3$, and wherein Q is as was previously defined. The phthalimide group is removed from products of general formula P2 by refluxing briefly for from 15 to 60 min in either concentrated hydrochloric acid, concentrated hydrochloric acid in acetic acid, 30% hydrobromic acid, or 48% hydrobromic acid. In each instance, the phthalic acid by-product is filtered from the resulting solution, after allowing to cool to room temperature. The volume is reduced and the product neutralized with either NaOH, $NaHCO_3$ or $Na_2CO_3$. Extraction into either ether or ethyl acetate and subsequent concentration in vacuo affords the product.

Products of general formula P3 are condensed with a reagent selected from either salicylaldehyde, 2-hydroxyacetophenone and 2-hydroxydiphenylketone, to afford products of general formula P4 (FIG. 1B, P4a–d), wherein either $R_2Ac$ is selected from either $N(CO)_2C_6H_4$, $OCOCH_3$ and $SCOCH_3$, or wherein $R_2$ is selected form either $CO_2H$ and $CO_2CH_3$, and wherein $R_3$ is selected from either H, $CH_3$ and $C_6H_5$, and wherein Q is as was previously defined. Condensation of products of general formula P3 with a reagent selected from either salicylaldehyde, 2-hydroxyacetophenone and 2-hydroxy-diphenylketone is achieved by refluxing in either methanol or 90% ethanol, at 60° C., for from 4 to 12 hours, the progress of the reaction being monitored by TLC. The product is concentrated in vacuo, then dried in a dessicator overnight.

Products of general formula P4 are deprotected by base catalyzed hydrolysis in warm aqueous $K_2CO_3$ or NaOH, for from 8 to 24 hours, to afford products of general formula P5 (FIG. 1B, P5b–d), wherein $R_3$ and Q are as were previously defined. The product is acidified with HCl, extracted into ethyl acetate, dried over anhydrous $MgSO_4$, and concentrated in vacuo. The protecting group is removed from a product of the general formula P4a by reaction with hydrazine hydrate in refluxing ethanol, for from 12 to 48 hours, to afford a product of the general formula P5a, wherein $R_3$ and Q are as were previously defined. The precipitated phthalhydrazide is filtered from solution, the solution concentrated, the product extracted into ethyl acetate, dried over anhydrous $MgSO_4$, and concentrated in vacuo.

The final product is prepared by activation of the amino, hydroxyl, thiol, and carboxylic acid groups associated with products of general formula P5. Amino groups may be activated by reaction with a reagent preferably selected from, but not limited to, bromoacetic anhydride, iodoacetic anhydride and maleic anhydride. Hydroxy groups may be activated by reaction with a reagent preferably selected from, but not limited to, 2,2,2-trifluroethaneulfonyl chloride, pentafluorobenzenesulfonyl chloride, toluenesulfonyl chloride and 2-cyanoethyl-N,N-diisopropylchlorophosphoramidite. Thiol groups may be activated by reaction with a reagent preferably selected from, but not limited to, 2-thiopyridone, 4-thiopyridone, and 3-nitro-2-mercaptopyridine. Carboxylic acid groups may be activated by reaction with a reagent preferably selected from either dicyclohexylcarbodiimide and 1-ethyl-3-(3-dimethylaminopropyl)carbodiimide, in the presence of a reagent preferably selected from, but not limited to, N-hydroxysuccinimide and N-hydroxysulfosuccinimide. Alternatively, carboxylic acid groups may be esterified with an alcohol preferably selected from either methanol and ethanol and then further functionalized by reaction with a reagent preferably selected from either hyrazine hydrate and hydroxylamine.

Products of General Formula I, wherein X is selected from either H, $CH_3$ and $C_6H_5$, and wherein Y is $CH_2$, are prepared as previously outlined by substituting potassium phthalimide for N-hydroxyphthalimide in the initial step of the synthesis.

Synthesis of Phenylboronic Acid Complexing Reagents of General Formula II

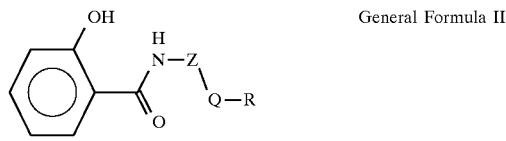

General Formula II

Figure 2A:
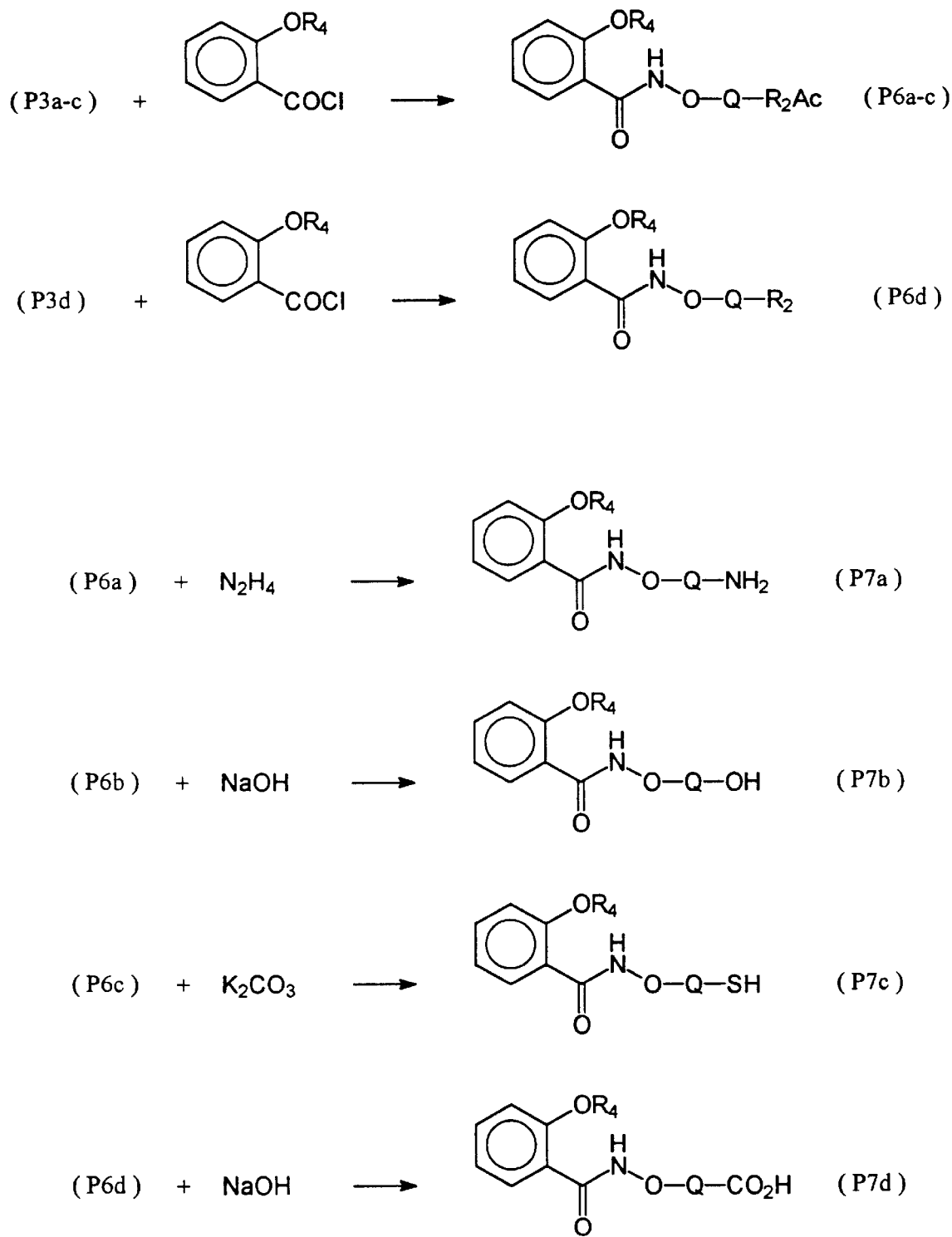
FIGS. 2A and 2B illustrate the synthesis of compounds of General Formula II, wherein Z is 0.
Figure 2B:
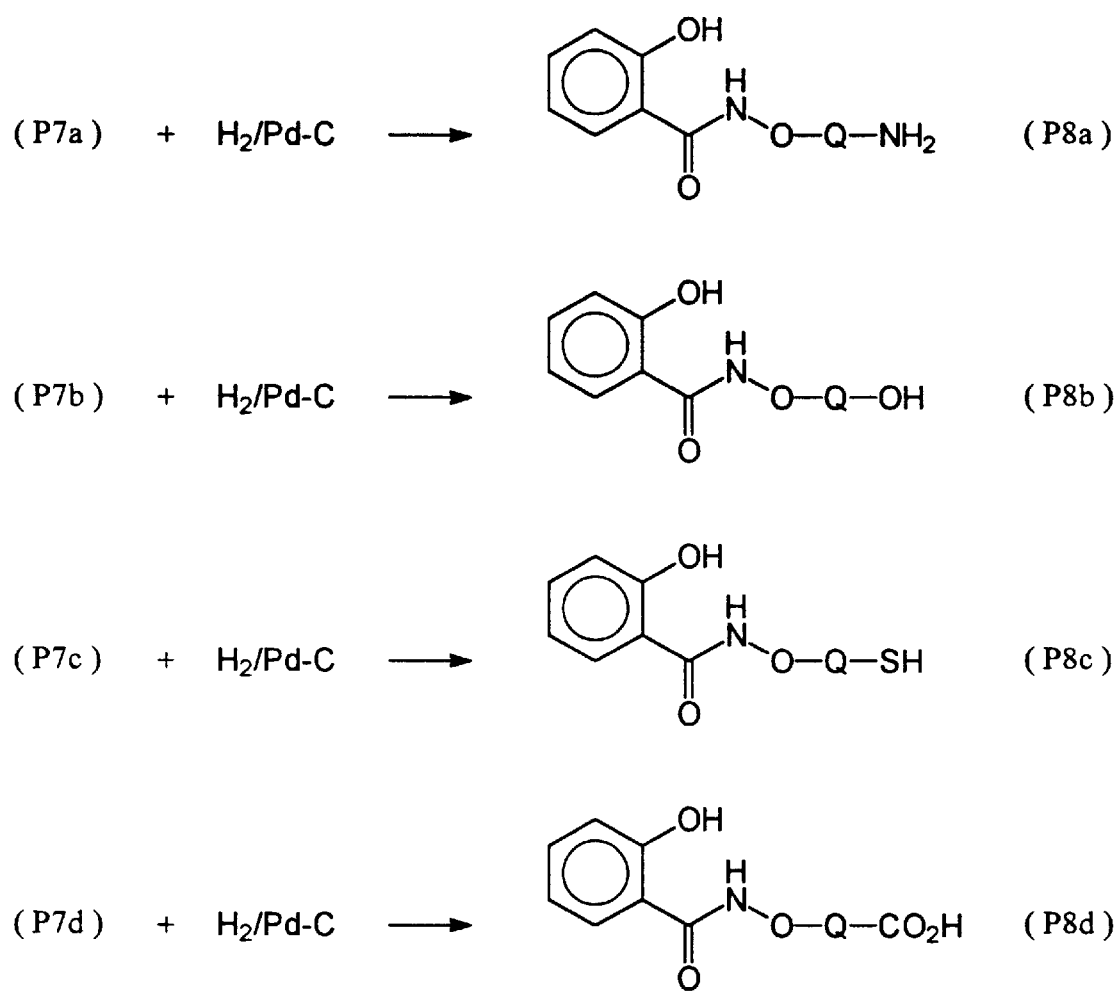

As illustrated in FIGS. 2A and 2B, reagents of General Formula II, wherein Z is O, are prepared in a manner analogous to that described above, the synthesis proceeding through the preparation of products of general formula P3 exactly as previously described.

Products of general formula P3 are condensed with a reagent preferably selected from, but not limited to, either 2-acetoxybenzoyl chloride and 2-benzyloxybenzoyl chloride, to afford products of general formula P6 (FIG. 2A, P6a–d), wherein $R_4$ is selected form either $COCH_3$ and $CH_2C_6H_5$, and wherein either $R_2Ac$ is selected from either $N(CO)_2C_6H_4$, $OCOCH_3$ and $SCOCH_3$, or $R_2$ is selected from either $CO_2H$ and $CO_2CH_3$, and wherein Q is as was previously defined. Condensation of products of general formula P3 with a reagent preferably selected from, but not limited to, either 2-acetoxybenzoyl chloride and 2-benzyloxybenzoyl chloride, is achieved by stirring in dichloro-methane containing one equivalent of triethylamine, for 1 hour at room temperature, the progress of the reaction being monitored by TLC. Triethylammonium hydrochloride is filtered from the solution. The filtrate is washed with water, dried over anhydrous $MgSO_4$, and concentrated in vacuo.

Compunds of general formula P6 are deprotected by base catalyzed hydrolysis in warm aqueous $K_2CO_3$ or NaOH, for from 8 to 24 hours, to afford products of general formula P7 (FIG. 2A, P7b–d), wherein Q is as was previously defined. The product is acidified with HCl, extracted into ethyl acetate, dried over anhydrous $MgSO_4$, and concentrated in vacuo. If an acetoxy protecting group had been employed to protect the phenolic hydroxyl group during the preparation of products of general formula P7, it would also be removed at this time, precluding the necessity for the synthetic step which follows. The protecting group is removed from a product of the general formula P6a by reaction with hydrazine hydrate ($N_2H_2.XH_2O$) in refluxing ethanol, for from 12 to 48 hours, to afford a product of the general fromula P7a, wherein $R_4$ is selected form either H and $CH_2C_6H_5$, and wherein Q is as was previously defined. The precipitated phthalhydrazide is filtered from solution, the solution concentrated, the product extracted into ethyl acetate, dried over anhydrous $MgSO_4$, and concentrated in vacuo.

Products of general formula P7 are further deprotected, if required, by removal of the benzyloxy protecting group by catalytic hydrogenation to afford products of general formula P8 (FIG. 2, P7a–d), wherein Q is as was previously defined. Catalytic hydrogenation proceeds over palladium-charcoal catalyst in anhydrous absolute ethanol, for from 2 to 12 hours. The catalyst is removed by filtration and the product concentrated in vacuo.

The final product is prepared by activation of the amino, hydroxyl, thiol, and carboxylic acid groups associated with products of general formula P8. Amino groups may be activated by reaction with a reagent preferably selected from, but not limited to, bromoacetic anhydride, iodoacetic anhydride and maleic anhydride. Hydroxy groups may be activated by reaction with a reagent preferably selected from, but not limited to, 2,2,2-trifluroethaneulfonyl chloride, pentafluorobenzenesulfonyl chloride, toluenesulfonyl chloride, and 2-cyanoethyl-N,N-diisopropylchlorophosphoramidite. Thiol groups may be activated by reaction with a reagent preferably selected from, but not limited to, 2-thiopyridone, 4-thiopyridone, and 3-nitro-2-mercaptopyridine. Carboxylic acid groups may be activated by reaction with a reagent preferably selected from either dicyclohexylcarbodiimide and 1-ethyl-3-(3-dimethylaminopropyl)carbodiimide, in the presence of a reagent preferably selected from, but not limited to, N-hydroxysuccinimide and N-hydroxysulfosuccinimide. Alternatively, carboxylic acid groups may be esterified with an alcohol preferably selected from either methanol and ethanol and then further functionalized by reaction with a reagent preferably selected from either hyrazine hydrate and hydroxylamine.

If activation of the final product is incompatible with the presence of the phenolic hydroxyl group associated with products of general formula P8, then products of general formula P7 may be first activated and the benzyloxy protecting group subsequently removed, provided that the activated form is stable toward catalytic hydrogenation.

Products of General Formula II, wherein group Z is $CH_2$ are prepared as previously outlined by substituting potassium phthalimide for N-hydroxyphthalimide in the initial step of the synthesis.

Bioconjugate Preparation

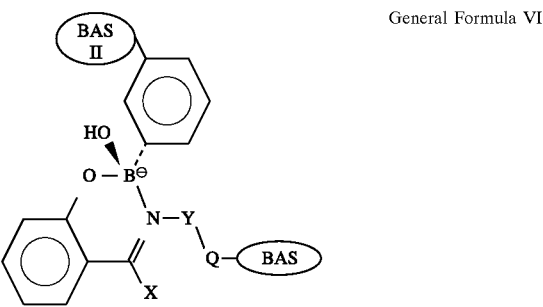

General Formula VI

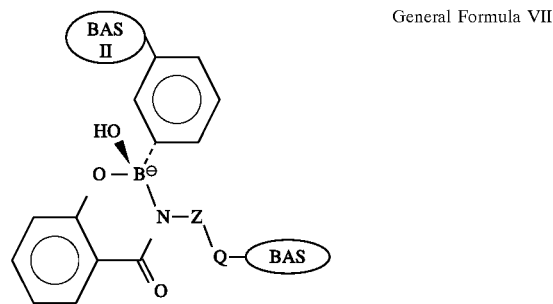

General Formula VII

Bioconjugates of General Formulas VI and VII may be prepared in buffered aqueous or aqueous/organic solutions. Preferred buffers include phosphate, carbonate, citrate and diglycine. Borate and Tris buffers should be avoided. The bioconjugate is formed within from 1 to 15 minutes at room temperature. The conjugation reaction (phenylboronic acid complexation) is insensitive to variations in ionic strength over the range 0.01 to 2 molar. Conjugation occurs rapidly at room temperature, and the stability of the conjugate increases with increasing temperature, being limited only by the volatility of the buffer at elevated temperature. The addition of organic solvents including acetonitrile, methanol, ethanol, isopropanol, butanol, N,N- dimethylformamide and dimethylsulfoxide serves to further stabilize conjugates.

Once formed, bioconjugates are stable upon removal of water, and can be purified by lyophilization. Additionally, the use of chaotropic reagents including urea, guanidine hydrochloride and formamide has no impact on the stability of conjugates. This is an important feature of this system in that prior art Avidin-Biotin and Digoxigenin-anti-Digoxigenin systems are incompatible with chaotropic reagents.

Example I

Figure 3:
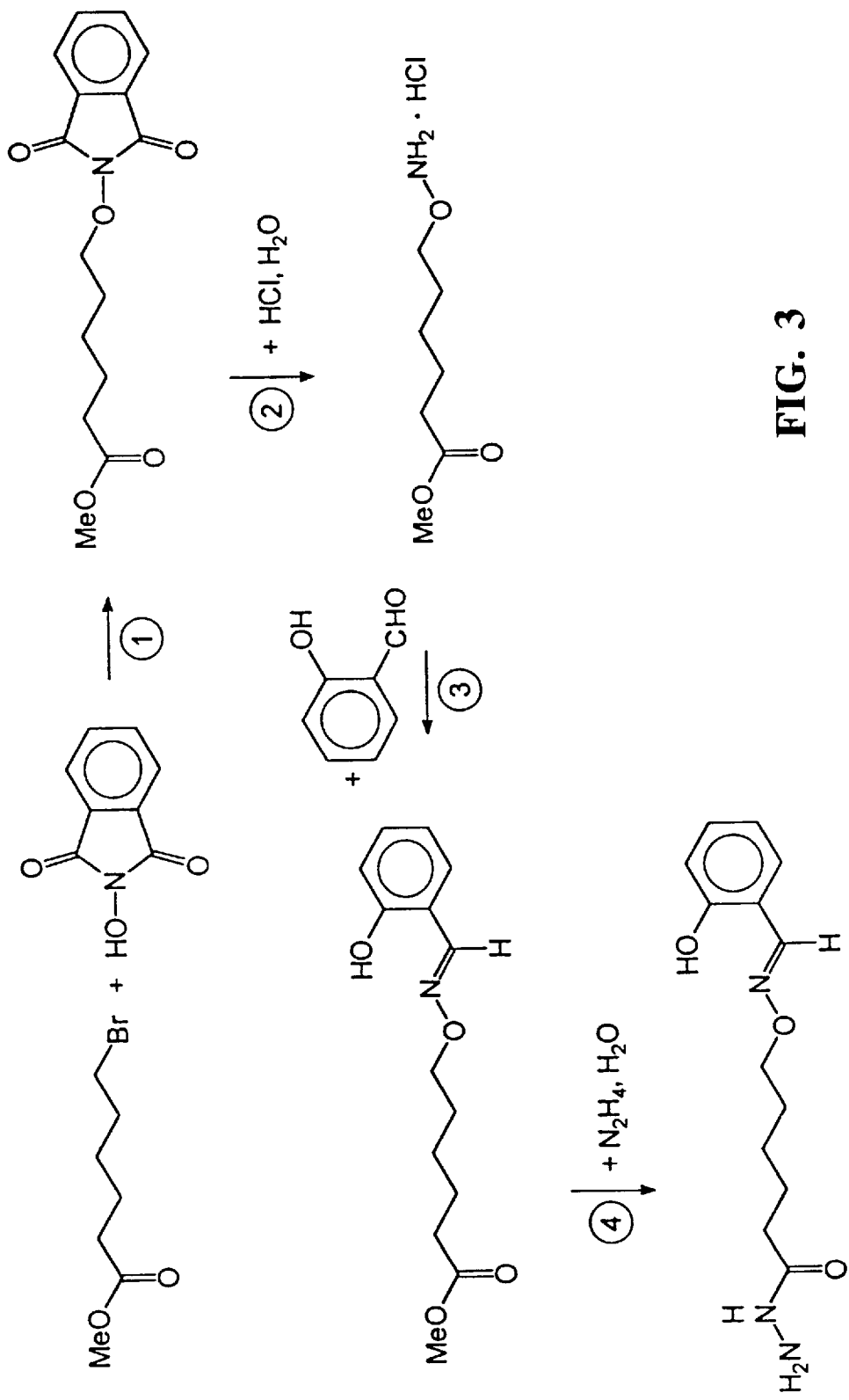
FIG. 3 illustrates the synthesis of an aldehyde reactive phenylboronic acid complexing reagent of General Formula I.
Figure 4:
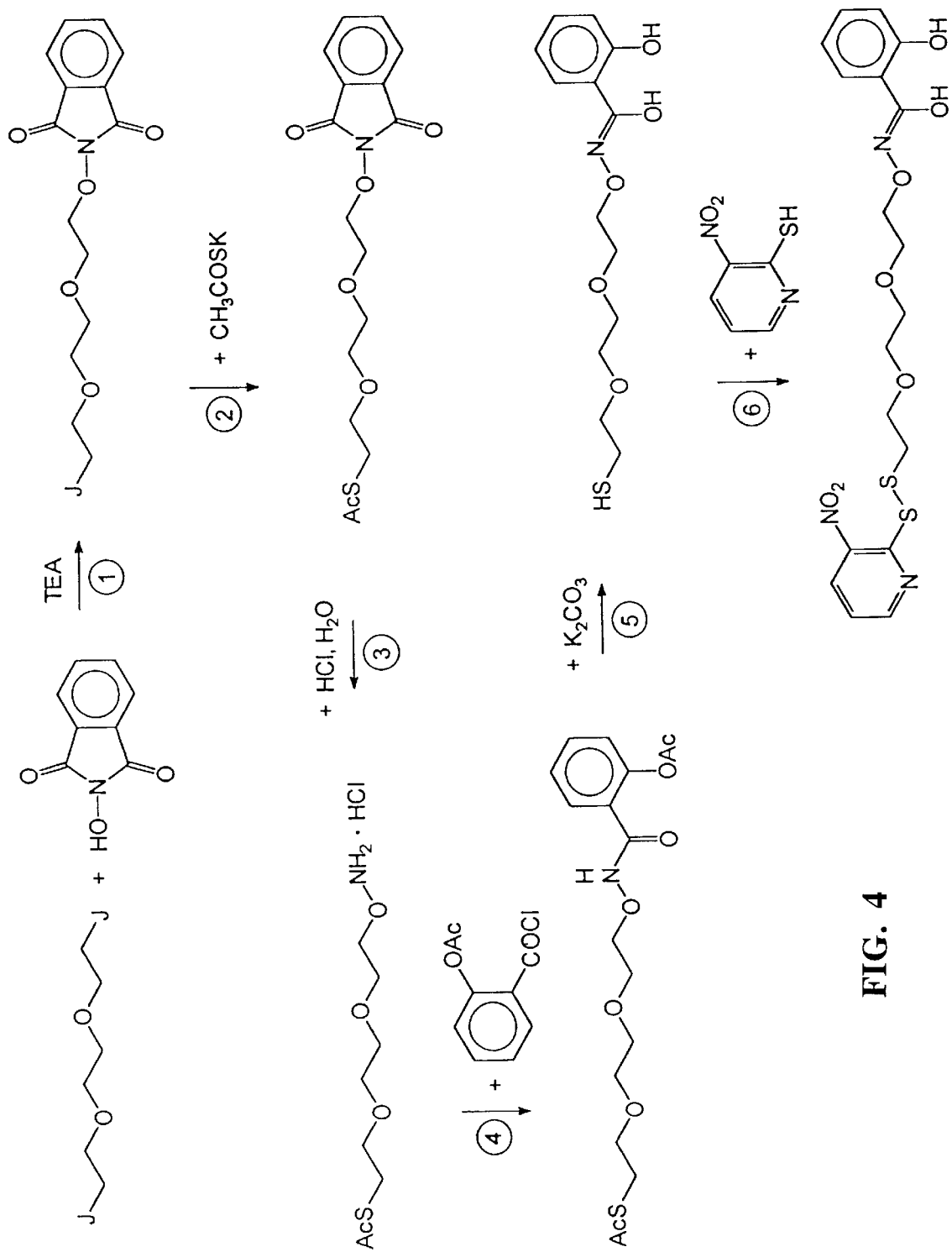
FIG. 4 illustrates the synthesis of a thiol reactive phenylboronic acid complexing reagent of General Formula II.

Preparation of An Aldehyde Reactive Phenylboronic Acid Complexing Reagent of General Formula I The synthesis of an aldehyde reactive phenylboronic acid complexing reagent of General Formula I is outlined in FIG. 3. In the initial step of the synthesis methyl 6-bromohexanoate is condensed with N-hydroxyphthalimide by stirring in dimethylformamide containing one equivalent of triethylamine for 24 hours. The product is precipitated by pouring into water, collected by filtration, washed with water, dried in a vacuum dessicator, and used without further purification.

In the second step of the synthesis the crude product obtained above is refluxed briefly in a mixture of acetic acid and concentrated hydrochloric acid. After cooling, the precipitated phthalic acid is filtered from solution and the filtrate concentrated and then coevaporated repeatedly from small volumes of water to remove traces of acids. Finally, the aminooxy hydrochloride product is neutralized with $NaHCO_3$, extrated in ethyl acetate, dried over anhydrous $MgSO_4$, and concentrated in vacuo.

In the third step of the synthesis the aminooxy product obtained above is condensed with one equivalent of 2-hydroxybenzaldehyde by refluxing for 6 hours in 90% ethanol, and then concentrated in vacuo, to afford the aldoxime.

Finally, the aldoxime product obtained above is treated with excess hydrazine hydrate by stirring overnight in methanol. The precipitated hydrazide aldoxime product is cooled on an ice bath, filtered from solution, redissolved in methanol, and then concentrated in vacuo.

Example II

Application of An Aldehyde Reactive Phenylboronic Acid Complexing Reagent

Glycoproteins, and particularly antibodies, may be conjugated with an aldehyde reactive phenylboronic acid complexing hydrazide reagent after treatment of the protein with from 5 to 20 mM sodium meta periodate ($NaIO_4$), in from 0.1 to 0.5M sodium acetate buffer at pH 5 to 6, containing up to 0.2M sodium chloride, at 0° C., for from 30 minutes to 4 hours. The excess periodate is removed by dialysis or desalting, and the activated protein, having pendant adjacent aldehyde moieties resulting from periodate oxidation of carbohydrate residues having adjacent coaxial 1,2-diol moities, is condensed with the hydrazide reagent, for from 1 to 24 hours at room temperature, to afford a semiconjugate having pendant phenylboronic acid complexing moieties covalently appended to the protein throught a Shiff base (an imine) type linkage. The stability of the linkage to the protein may be increased, if desired, by mild sodium cyanoborohydride reduction of the Schiff base to the corresponding alkylamine.

It is important to note that periodate oxidation of a glycoprotein activates the protein toward reaction with a hydrazide type reagent while simultaneously removing most naturally occuring phenylboronic acid complexing sites (coaxial 1,2-diols) associated with glycoproteins.

Example III

Figure 5:
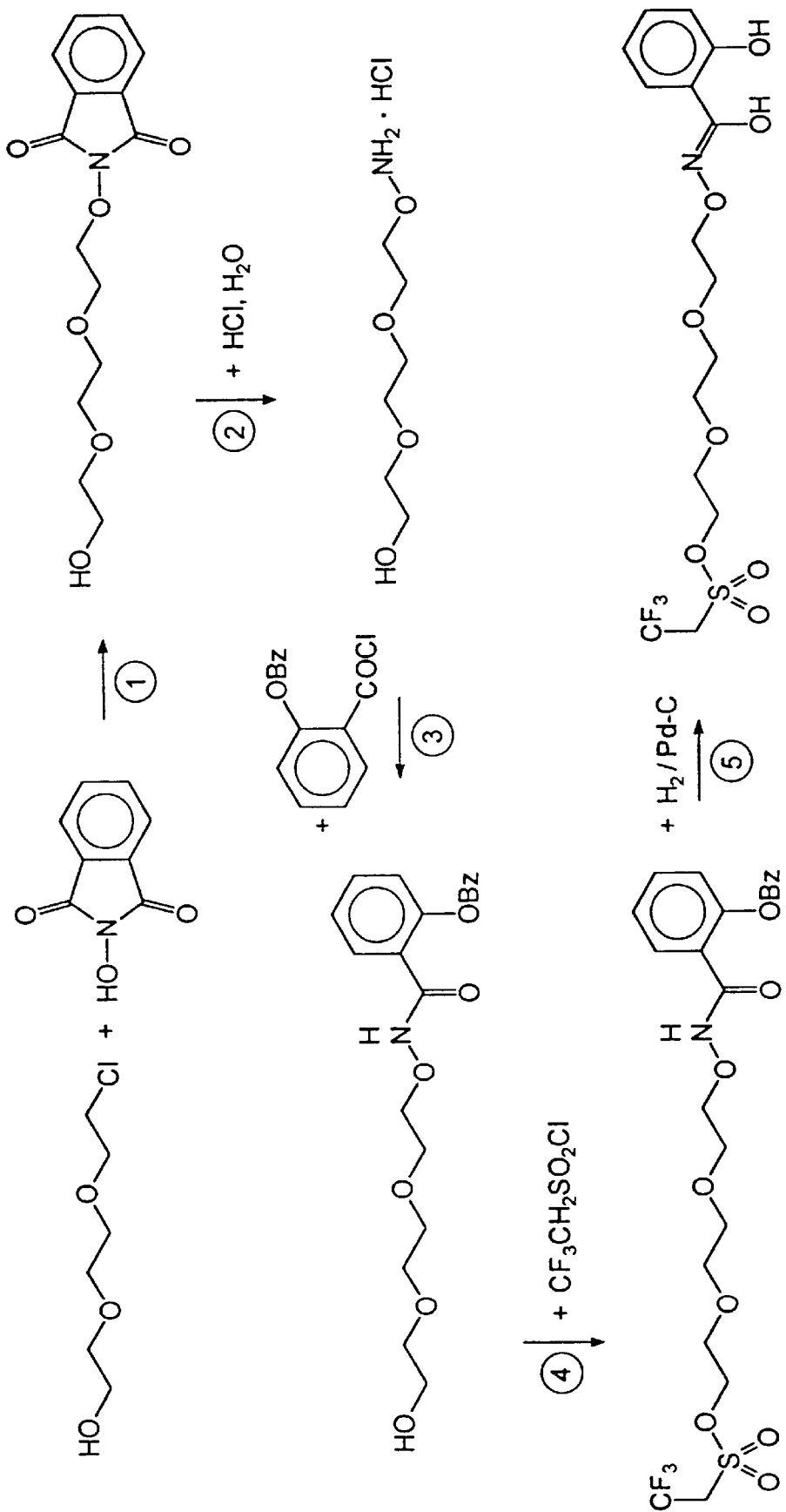
FIG. 5 illustrates the syntheis of an amine reactive phenylboronic acid complexing reagent of General Formula II.

Preparation of A Thiol Reactive Phenylboronic Acid Complexing Reagent of General Formula II The synthesis of a thiol reactive phenylboronic acid complexing reagent of general formula II is outlined in FIG. 5. In the initial step of the synthesis 1,2-bis-(2-iodoethoxy) ethane is condensed with N-hydroxyphthalimide by refluxing in dimethylformamide containing one equivalent of triethylamine for 3 days. The product is precipitated by pouring into water, collected by filtration, washed with water, dried in a vacuum dessicator, and used without further purification.

In the second step of the synthesis the crude product obtained above, in absolute ethanol, is treated with excess potassium thioacetate and the resulting yellow suspension heated at reflux for 1 hour. The mixture is cooled, filtered, and concentrated in vacuo, and the slurry partitioned between ethyl acetate and water. The combined ethyl acetate layers were washed with saturated aqueous $NaHCO_3$ solution, and water, dried over anhydrous $MgSO_4$, and concentrated in vacuo.

In the third step of the synthesis the product obtained above is refluxed briefly in a mixture of acetic acid and concentrated hydrochloric acid. After cooling, the precipitated phthalic acid is filtered from solution and the filtrate concentrated and then coevaporated repeatedly from small volumes of water to remove traces of acids. Finally, the aminooxy hydrochloride product is neutralized with $NaHCO_3$, extrated in ethyl acetate, dried over anhydrous $MgSO_4$, and concentrated in vacuo.

In the fourth step of the synthesis the aminooxy product obtained above is condensed with one equivalent of 2-acetoxybenzoyl chloride by stirring for 1 hour at room temperature in dichloromethane containing one equivalent of triethylamine, the progress of the reaction being monitored by TLC. Triethylammonium hydrochloride is filtered from the solution, and the filtrate washed with water, dried over anhydrous $MgSO_4$, and concentrated in vacuo.

In the fifth step of the synthesis the 2-acetoxybenzohydroxamic acid product obtained above, in absolute methanol was throughly degassed with nitrogen and treated with one equivalent of anhydrous $K_2CO_3$, and the resulting yellow suspension was stirred vigorously for 12 hours. The suspension was filtered and concentrated in vacuo.

Finally, the mercapto 2-hydroxybenzohydroxamic acid product is treated with a solution of (methoxycarbonyl) sulfenyl chloride in dry, degassed methanol by stirring at 0° C. for 1 hour, and the methanol removed in vacuo. The product is again dissolved in degassed methanol and treated with one equivalent of 3-nitro-2-mercaptopyridine by stirring at room temperature for 12 hours. The mixture is filtered to remove unreacted 3-nitro-2-mercaptopyridine, and the product concentrated in vacuo.

Example IV

Application of A Thiol Reactive Phenylboronic Acid Complexing Reagent

Proteins containing disulfide bonds may be conjugated with a thiol reactive phenylboronic acid complexing reagent.

Disulfide bonds are first reduced, by reaction with 2-mercaptoethanol or dithiothreitol, in alkaline aqueous solution which has been throughly degassed. The excess reducing reagent is removed by dialysis or desalting, and the protein reacted with the thiol reactive reagent in throughly degassed alkaline aqueous solution, under nitrogen, overnight at 4° C., to afford a semiconjugate having pendant phenylboronic acid complexing moieties covalently appended to the protein throught disulfide linkages. Upon completion of the reaction, the excess reagent is removed by desalting or by thiol exchange chromatography. The phenylboronic acid complexing moities may be removed from the semiconjugate by reduction of the disulfide bond as described above. In this manner, bioconjugates involving semiconjugates prepared from thiol reactive phenylboronic acid complexing reagents may be cleaved.

Example V

Figure 6:
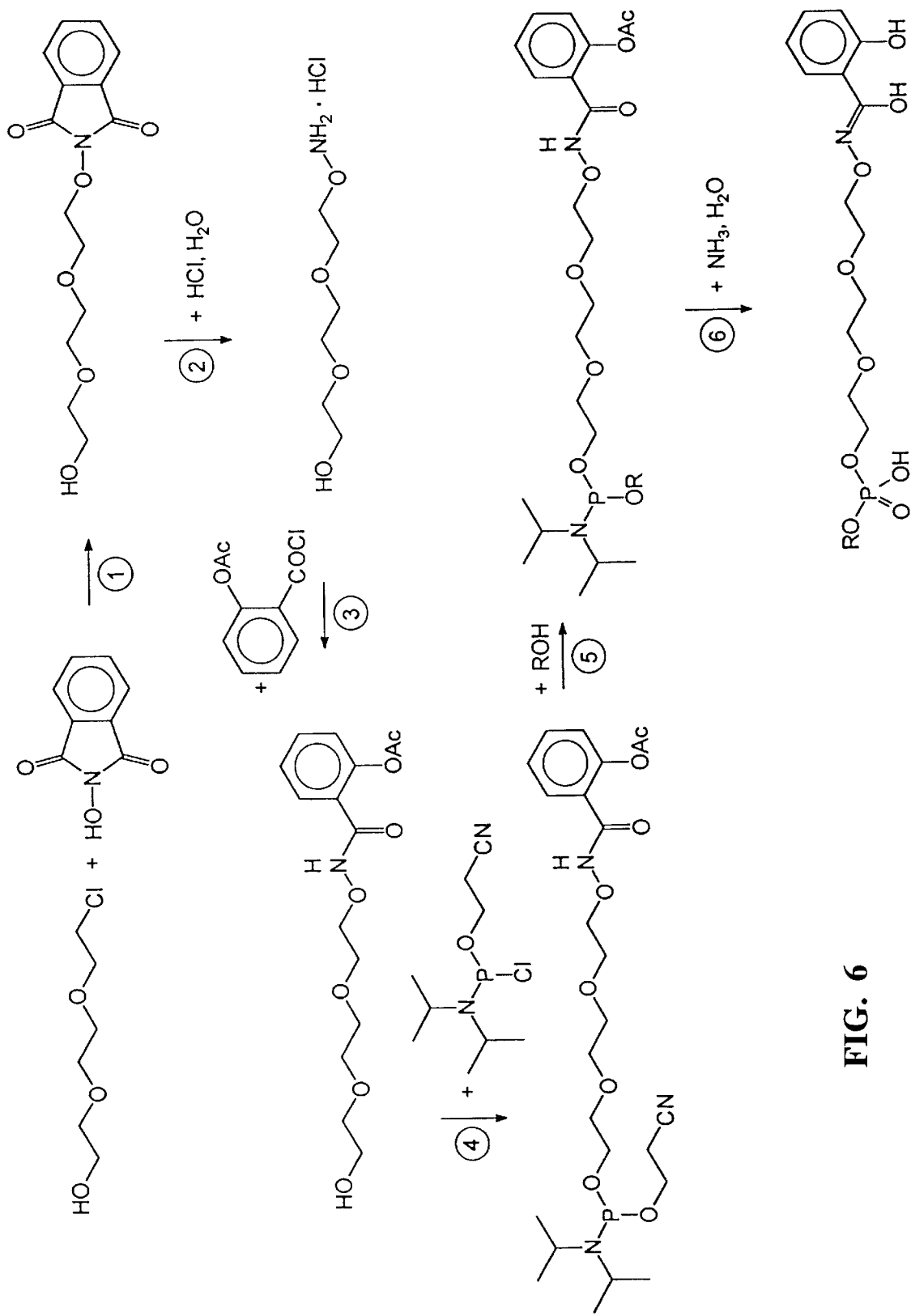
FIG. 6 illustrates the synthesis of a synthetic oligonucleotide reactive phenylboronic acid complexing reagent of General Formula II.

Preparation of An Amine Reactive Phenylboronic Acid Complexing Reagent of General Formula II The synthesis of an amine reactive phenylboronic acid complexing reagent of general formula II is outlined in FIG. 6. In the initial step of the synthesis 2-[2-(2-chloroethoxy) ethoxy]ethanol is condensed with N-hydroxyphthalimide by refluxing in dimethylformamide containing one equivalent of triethylamine for 2 days. The product is precipitated by pouring into water, collected by filtration, washed with water, dried in a vacuum dessicator, and used without further purification.

In the second step of the synthesis the crude product obtained above is refluxed briefly in a mixture of acetic acid and concentrated hydrochloric acid. After cooling, the precipitated phthalic acid is filtered from solution and the filtrate concentrated and then coevaporated repeatedly from small volumes of water to remove traces of acids. Finally, the aminooxy hydrochloride product is neutralized with NaHCO$_3$, extrated in ethyl acetate, dried over anhydrous MgSO$_4$, and concentrated in vacuo.

In the third step of the synthesis the hydroxy aminooxy product obtained above is condensed with one equivalent of 2-benzyloxybenzoyl chloride by stirring for 1 hour at room temperature in dichloromethane containing one equivalent of triethylamine, the progress of the reaction being monitored by TLC. Triethylammonium hydrochloride is filtered from the solution, and the filtrate washed with water, dried over anhydrous MgSO$_4$, and concentrated in vacuo.

In the fourth step of the synthesis the hydroxy 2-benzyloxybenzohydroxamic acid product obtained above is condensed with one equivalent of 2,2,2-trifluoroethanesulfonyl chloride by stirring for 1 hour at room temperature in acetonitrile containing one equivalent of triethylamine. Triethylammonium hydrochloride is filtered from the solution, and the filtrate washed with water, dried over anhydrous MgSO$_4$, and concentrated in vacuo.

Finally, the benzyloxy protecting group is removed by catalytic hydrogenation over palladium-charcoal for 8 hours in anhydrous absolute ethanol. The catalyst is removed by filtration and the product concentrated in vacuo.

Example VI

Application of An Amine Reactive Phenylboronic Acid Complexing Reagent

Proteins may be conjugated with amine reactive phenylboronic acid complexing reagents by reaction with the side-chain s-amino groups of lysine residues, to afford a semiconjugate having pendant phenylboronic acid complexing moities covalently appended to the protein through stable sulfonamide bonds. Alkaline aqueous buffers should be employed so as to insure that the amino group is unprotonated. Primary amine containing buffers including Tris and glycine must be avoided, so as to avoid cross-reactivity. Solid-phase supports having pendant primary amine moities may be functionalized, in an analogous manner, by reaction with phenylboronic acid complexing reagents to afford solid-phase supports having pendant phenylboronic acid complexing moities.

Example VII

Preparation of A Synthetic Oligonucleotide Reactive Phenylboronic Acid Complexing Reagent of General Formula II The synthesis of a synthetic oligonucleotide reactive phenylboronic acid complexing reagent of general formula II is outlined in FIG. 7. In the initial step of the synthesis 2-[2-(2-chloroethoxy)ethoxy]ethanol is condensed with N-hydroxyphthalimide by refluxing in dimethylformamide containing one equivalent of triethylamine for 2 days. The product is precipitated by pouring into water, collected by filtration, washed with water, dried in a vacuum dessicator, and used without further purification.

In the second step of the synthesis the crude product obtained above is refluxed briefly in a mixture of acetic acid and concentrated hydrochloric acid. After cooling, the precipitated phthalic acid is filtered from solution and the filtrate concentrated and then coevaporated repeatedly from small volumes of water to remove traces of acids. Finally, the aminooxy hydrochloride product is neutralized with NaHCO$_3$, extrated in ethyl acetate, dried over anhydrous MgSO$_4$, and concentrated in vacuo.

In the third step of the synthesis the hydroxy aminooxy product obtained above is condensed with one equivalent of 2-acetoxybenzoyl chloride by stirring for I hour at room temperature in dichloromethane containing one equivalent of triethylamine, the progress of the reaction being monitored by TLC. Triethylammonium hydrochloride is filtered from the solution, and the filtrate washed with water, dried over anhydrous MgSO$_4$, and concentrated in vacuo.

In the fourth step of the synthesis the hydroxy 2-acetoxybenzohydroxamic acid product obtained above is condensed with one equivalent of 2-cyanoethyl-N,N-diisopropylchlorophosphoramidite by stirring for 1 hour at room temperature in aceto-nitrile containing one equivalent of triethylamine. Triethylammonium hydrochloride is filtered from the solution, and the filtrate washed with water, dried over anhydrous MgSO$_4$, and concentrated in vacuo.

In the fifth step of the synthesis the 2-cyanoethyl-N,N-diisopropylphosphoramidite 2-acetoxybenzohydroxamic acid obtained above is dissolved in acetonitrile and placed in the auxiliary reservoir of an automated olgionucleotide synthesizer. The product is condensed with the free 5'-OH end of an immobilized synthetic oligonucleotide undergoing synthesis by pyridine catalyzed reaction with the 2-cyanoethyl-N,N-diisopropylphosphoramidite reagent in acetonitrile. The solid-phase synthesis is terminated in this manner. In the final step of the syntheis, the product is cleaved from the glass solid-phase support by ammonia lysis overnight with concentrated ammonium hydroxide at from 50° to 60° C. Ammonia lysis removes the product from the solid-phase support, as well as removing all acyl protecting groups including the acetoxy group associated with the 2-acetoxybenzohydroxamic acid functionality. The product is concentrated by removal of ammonia on a speedvac, and then purified by reverse-phase high performance liquid chromatography (HPLC).

Example VIII

Application of A Synthetic Oligonucleotide Reactive Phenylboronic Acid Complexing Reagent Synthetic oligonucleotides may be conjugated with a 2-cyanoethyl-N,N-diisopropylphosphoramidite phenylboronic acid complexing reagents, during the final step of an automated solid-phase oligonucleotide synthesis, to afford synthetic oligonucleotides having 5'-pendant phenylboronic acid complexing moities.

I claim:

1. A phenylboronic acid complexing reagent (PBCR) for conjugating biologically active molecules through a boronic acid complex, said phenylboronic acid complexing reagent having General Formula II:

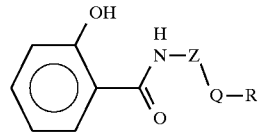

wherein group Z is selected from O and CH$_2$; group Q is a spacer which is from 2 to 12 carbon equivalents in length, and which may contain intermediate amide and/or ether functionalities; and group R is a reactive electrophilic moiety suitable for conjugation of the phenylboronic acid complexing reagent with a biological macromolecular species, low molecular weight species or solid phase support having a reactive pendant nucleophilic moiety.

2. The phenylboronic acid complexing reagent of claim 1 wherein R is an electrophilic moiety selected from the group consisting of hydrazide, isothiocyanate, N-hydroxysuccinimidyl ester, imidate ester, tresyl, bromoacetamide, iodoacetamide, maleimide and 2-cyanoethyl-N,N-diisopropylphosphoramidite ester moieties.

3. The phenylboronic acid complexing reagent of claim 1 wherein group Z is O.

4. The phenylboronic acid complexing reagent of claim 1 wherein Q is selected from (CH$_2$)$_n$, wherein n=2 to 6, and (CH$_2$CH$_2$O)$_n$, wherein n=2 to 4.

5. A semiconjugate of a bioactive species with a phenylboronic acid complexing reagent for conjugating to other biologically active species through a boronic acid complex, said semiconjugate having the general formula:

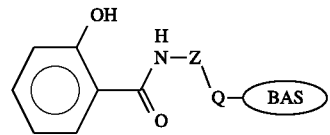

where:

Z=O or CH$_2$

Q=a spacer a spacer which is from 2 to 12 carbon equivalents in length, and which may contain intermediate amide and/or ether functionalities, and BAS=a biological macromolecular species, low molecular weight species or solid-phase support having pendant nucleophilic moieties.

* * * * *

UNITED STATES PATENT AND TRADEMARK OFFICE
CERTIFICATE OF CORRECTION

PATENT NO. : 5,852,178
DATED : December 22, 1998
INVENTOR(S) : Stolowitz

It is certified that error appears in the above-identified patent and that said Letters Patent is hereby corrected as shown below:

<u>Title page,</u>
Item [56], References Cited, U.S. PATENT DOCUMENTS, please delete the three occurrences of "Stolomitz" and insert in each instance -- Stolowitz --.
OTHER PUBLICATIONS, "Kawasaki et al.", reference, after "*Abstracts*;" please insert -- vol. --.
Brief Description of the Drawings, Figure 5, please delete "syntheis" and insert -- synthesis --.

Signed and Sealed this

Twenty-ninth Day of June, 2004

JON W. DUDAS
*Acting Director of the United States Patent and Trademark Office*